(12) United States Patent
Drobe

(10) Patent No.: US 8,845,101 B2
(45) Date of Patent: Sep. 30, 2014

(54) AMETROPIA PROGRESSION INDICATING DEVICE

(75) Inventor: Bjoern Drobe, Charenton le Pont (FR)

(73) Assignee: Essilor International (Compagnie Generale d'Optique), Charenton le Pont Cedex (FR)

(*) Notice: Subject to any disclaimer, the term of this patent is extended or adjusted under 35 U.S.C. 154(b) by 120 days.

(21) Appl. No.: 13/381,645

(22) PCT Filed: Jun. 24, 2010

(86) PCT No.: PCT/EP2010/059018
§ 371 (c)(1),
(2), (4) Date: Dec. 29, 2011

(87) PCT Pub. No.: WO2011/000777
PCT Pub. Date: Jan. 6, 2011

(65) Prior Publication Data
US 2012/0099079 A1    Apr. 26, 2012

(30) Foreign Application Priority Data

Jun. 30, 2009 (EP) .................................. 09305630

(51) Int. Cl.
*A61B 3/02* (2006.01)
*G02C 5/00* (2006.01)
*G02C 7/02* (2006.01)
*A61B 3/04* (2006.01)

(52) U.S. Cl.
USPC ......... 351/222; 351/41; 351/159.01; 351/227

(58) Field of Classification Search
USPC ......... 351/200, 205, 222, 227, 228, 229, 230, 351/246, 41, 159
See application file for complete search history.

(56) References Cited

U.S. PATENT DOCUMENTS

| | | | |
|---|---|---|---|
| 2,893,288 A * | 7/1959 | Sheridan | ........................ 351/234 |
| 4,329,570 A | 5/1982 | Koll | |
| 4,882,472 A | 11/1989 | Sigman et al. | |
| 5,357,294 A * | 10/1994 | Shimizu et al. | ................ 351/212 |
| 5,717,193 A | 2/1998 | Marcelo | |

FOREIGN PATENT DOCUMENTS

| | | |
|---|---|---|
| DE | 298 04 586 | 6/1998 |
| WO | WO 2005/081172 | 9/2005 |

* cited by examiner

*Primary Examiner* — Dawayne A Pinkney
(74) *Attorney, Agent, or Firm* — Cozen O'Connor

(57) ABSTRACT

An indicating device (10, 100) for indicating the ametropia progression of a wearer over a predetermined period of time according to at least the type of ophthalmic lens the wearer may use. The device comprises first (12, 120) and second (14, 140) members connected together in a moveable manner. The first member (12, 120) has a first field (22, 220) including a plurality of values of input data and a second field (24, 240) including a plurality of values of output data representative of the ametropia of a wearer. The second member (14, 140) has at least a selection mean (40, 400) and an indication mean. The selection means (40, 400) is arranged to select among movement of the second member (14, 140) a value of the input data corresponding to a wearer. The indication means (28, 26, 30, 32, 36, 38, 280, 260, 300, 320, 360, 380) is associated with a type of ophthalmic lens and arranged to indicate among movement of the second member (14, 140) the value of the output data on the first member (12, 120) corresponding to the ametropia of the wearer after the predetermined period of time.

7 Claims, 3 Drawing Sheets

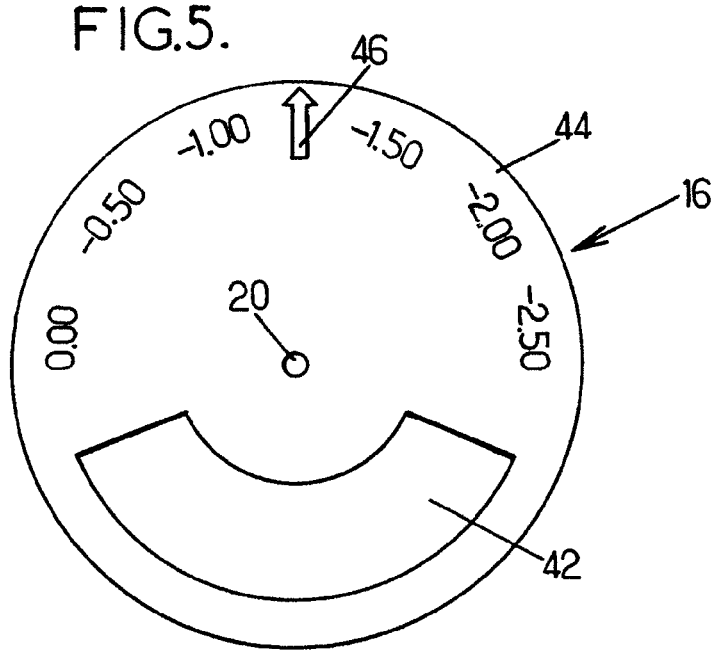
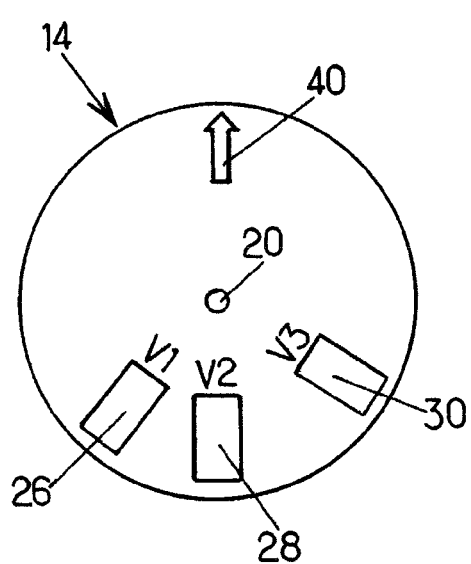
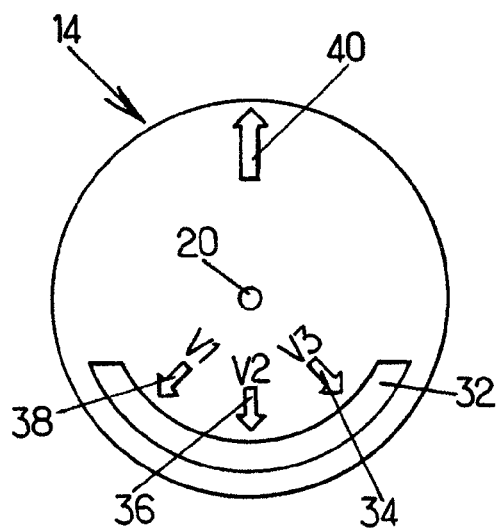

AMETROPIA PROGRESSION INDICATING DEVICE

RELATED APPLICATION

This is a U.S. national stage of application No. PCT/EP2010/059018, filed on 24 Jun. 2010.

This application claims the priority of European Application No. 09305630.7, filed 30 Jun. 2009 the entire content of which is hereby incorporated by reference.

FIELD OF THE INVENTION

The present invention relates to an indicating device. More particularly, the present invention relates to an indicating device for indicating the ametropia progression of a wearer over a predetermined period of time according to at least the type of ophthalmic lens the wearer may use.

SUMMARY OF THE INVENTION

It is an object of the invention to provide a simple, reliable and inexpensive device for indicating the ametropia progression of a wearer over a predetermined period of time according to the type of ophthalmic lens the wearer may use. Typically, the device may be used to help a user choose a type of ophthalmic lens by indicating the progression of the ametropia of a wearer according to the type of ophthalmic lens the wearer may use.

For this purpose, one aspect of the invention is directed to an indicating device for indicating the ametropia progression of a wearer over a predetermined period of time according to at least the type of ophthalmic lens the wearer may use, wherein the device comprises first and second members connected together in a moveable manner, the first member having a first field including a plurality of values of input data and a second field including a plurality of values of output data representative of the ametropia of a wearer, the second member having at least a selection mean and an indication mean, the selection mean being arranged to select among movement of the second member a value of the input data corresponding to a wearer and the indication mean being associated with a type of ophthalmic lens and arranged to indicate among movement of the second member the value of the output data on the first member corresponding to the ametropia of the wearer after the predetermined period of time.

It will be appreciated that the indicating device according to the invention can be used to quickly indicate the ametropia progression of a wearer. Such an indicating device may be useful to optical practitioner and ophthalmic lens wearer to choose the type of ophthalmic lens to use.

According to further embodiments of the invention, the indicating device according to the invention may comprise the following features alone or in combination:

the indicating device further comprises a third member connected to the first and second members in a moveable manner, the third member comprises:

a field including a plurality of values of second input data, a selecting mean arranged to select among movement of the third member a value of the input data from the first member, and an opening arranged to display at least a part of the second field of the first member among movement of the third member;

the input data are selected among one or a combination of the following data consisting of:

the age of the first optical correction,
the actual age of the wearer,
the actual refraction value of the wearer,
the ethnic group of the wearer,
the medical treatment the wearer may use,
the number of reading hours per day,
the reading distance of the wearer, and
the type of lighting the wearer may use;

the output data are selected among one or a combination of the following data consisting of:

the ametropia value after a given period of time/at a given age,
the risk of eye pathology,
the risk of car accident, and
the risk of falling.

the selection mean and/or indication mean comprise a window dimensioned for displaying a single value of the input data and/or output data;

the selection mean and/or indication mean comprise an arrow arranged to displaying a single value of the input data and/or output data;

the first, second and third members are connected together for rotating about an axis;

the first, second and third members are connected together for translation about a longitudinal axis of the indicating device.

BRIEF DESCRIPTION OF THE DRAWINGS

The invention will now be described with reference to the accompanying drawings, in which:

FIG. 5 shows a frontal view of a third disc of an indicating device as represented on FIG. 1.

DETAILED DESCRIPTION OF THE DRAWINGS

For reasons of clarity, the elements shown on the figures are not necessarily to scale.

Figure 1:
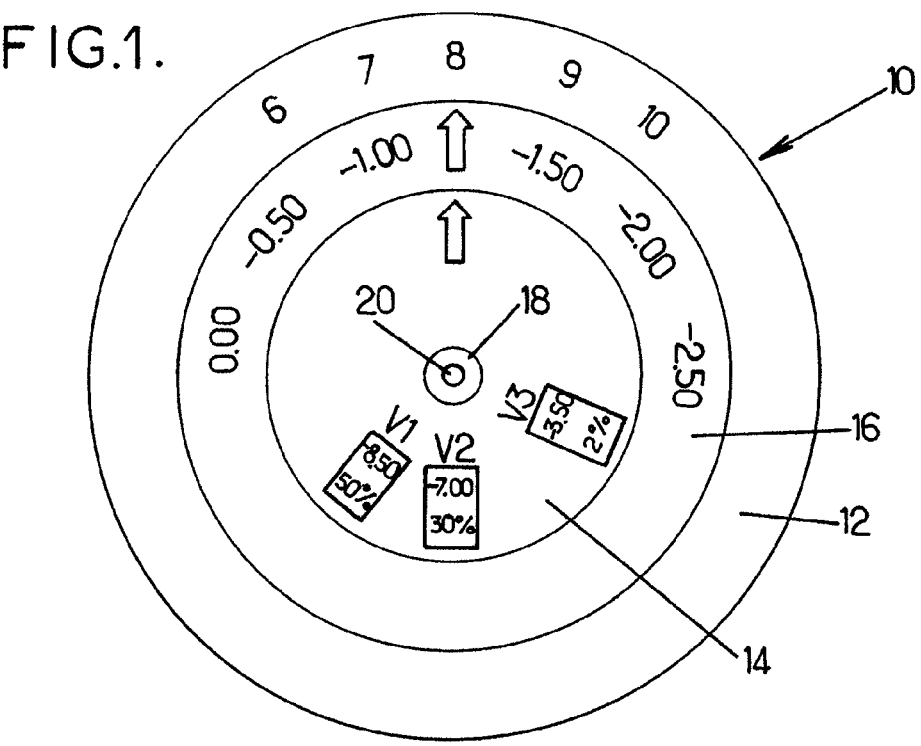
FIG. 1 shows a frontal view of a indicating device according to a first embodiment of the invention.
Figure 2:
FIG. 2 shows a side view of an indicating device as represented on FIG. 1.

The indicating device 10 represented on FIGS. 1 and 2 is an indicating device according to a first embodiment of the invention. The indicating device 10 is for the purpose of indicating the ametropia of wearer at the age of eighteen according to the value of the ametropia at a selected age.

According to the first embodiment of the invention represented on figures to 5 the first, second and third members of the indicating device are discs.

The indicating device 10 includes a first disc 12, a second disc 14, a third disc 16 and a pin 18 for pivotally connecting the first 12, second 14 and third 16 discs together for rotation about an axis 20.

Figure 3:
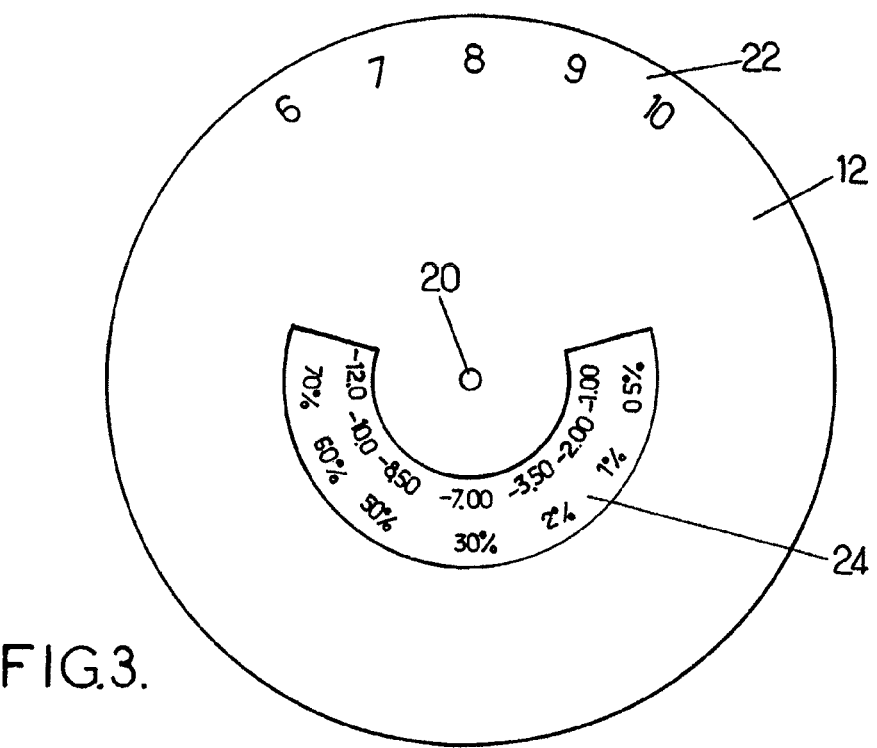
FIG. 3 shows a frontal view of a first disc of an indicating device as represented on FIG. 1, FIGS. 4a and 4b show a frontal view of different embodiments of second discs of an indicating device as represented on FIG. 1.

FIG. 3 represents an arrangement of the upper face of the first disc 12 of an indicating device 10 as represented on FIGS. 1 and 2. The upper face of the first disc 12 comprises a first field 22 comprising a plurality of values of an input data.

The input data may be any type of data that has an impact on the ametropia progression. The input data represented in the first field 22 may be selected among the following list consisting of:

the age of the first optical correction,
the ethnic group of the wearer,
the medical treatment the wearer may use,
the number of reading hours a day,
the reading distance of the wearer, and
the type of lighting the wearer may use.
the actual age of the wearer,
the actual refraction value of the wearer.

According to the embodiment of the invention represented on FIG. 3, the input data represented in the first field 22 represent the age of the wearer.

The upper face of the first disc 12 also comprises a second field 24 comprising a plurality of values of output data.

The output data may be any type of data that may be related to the ametropia of a wearer. The output data represented in the second field 24 may be selected among the following list consisting of:

the ametropia value after a given period of time, for example the ametropia at the age of eighteen,
the risk of eye pathology,
the risk of car accident, and
the risk of falling.

According to the embodiment of the invention represented on FIG. 3, the output data represented in the second field 24 represent the ametropia value and the risk of eye pathology of the wearer at the age of eighteen.

The first 22 and second 24 fields comprise part of an annular region of the upper face of the first disc 12, centered on the axis 20. The second field 24 has a smaller radius than the first field 22.

FIGS. 4a and 4b represent two arrangements of the upper face of the second disc 14 of an indicating device 10 represented on FIGS. 1 and 2.

The upper face of the second disc 14 represented on FIG. 4a comprises a first 26, second 28 and third 30 windows. The first 26, second 28, and third 30 windows are spaced from the axis 20 by a radial distance which is substantially the same as the radial distance of the second field 24 of the first disc 12. The first 26, second 28 and third 30 windows correspond to different type of ophthalmic lenses the wearer may use.

Alternatively as represented on FIG. 4b, the upper face of the second disc 14 may comprise a large window 32. The large window 32 is spaced from the axis 20 by a radial distance which is substantially the same as the radial distance of the second field 24 of the first disc 12. The upper face of the second disc 14 may also comprise first 34, second 36 and third 38 arrows pointing a specific part of the large window 32 in radial directions. The first 34, second 36 and third 38 arrows correspond to different type of ophthalmic lenses the wearer may use.

The upper face of the second disc 14 also comprises a fourth arrow 40 pointing to the outer circumference of the second disc 14. The fourth arrow 40 is placed on the outer part of the second disc 14.

The windows 26, 28, 30 and 32 and the arrows 34, 36, 38 correspond to indication means associated with a type of ophthalmic lens and arranged so that when the fourth arrow 40 indicates an input value, the output values corresponding to the different ophthalmic lenses are displayed in the first 26, second 28 and third 30 windows and/or pointed by the first 34, second 36 and third 38 arrows.

As represented on FIG. 5, the third disc 16, comprises a single composite window 42, a field 44 and a selecting mean 46.

The single composite window 42 is spaced from the axis 20 by a radial distance which is the same as the radial distance of the second field 24 of the first disc 12.

The field 44 is part of an annular region of the upper face of the third disc 16, centred on the axis 20. The field 44 comprises a plurality of values of an input data selected among the same list as the input data of the first field 22 of the first disc 12.

As represented on FIG. 5, the selecting mean 46 may be an arrow pointing in the outer circumference of the third disc 16. Alternatively, the selecting mean 46 may be a window in the outer circumference of the third disc 16.

According to an embodiment of the invention, the second field 24, 12 and the indication means 26, 28, 30, 32, 34, 36, 38 of the second disc 14 are arranged so that the ratio between the value of the output data represented in the second field 24 of the first disc 12 corresponding to a first type of ophthalmic lenses and the value of the output data represented in the second field 24 of the first disc 12 corresponding to a second type of ophthalmic lenses is constant independently of the value of the input data selected by the selection means 40 and 46.

According to an embodiment of the invention not represented, the indicating device may comprise only the first 14 and second 16 discs.

Figure 6:
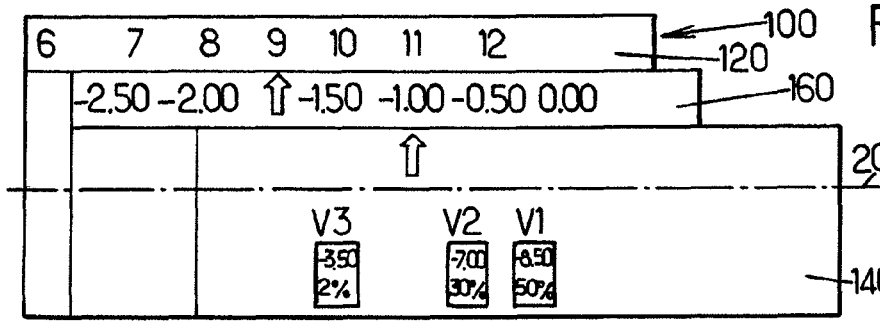
FIG. 6 shows a frontal view of a indicating device according to a second embodiment of the invention.

According to an embodiment of the invention represented on FIG. 6, the indicating device may have a rectangular shape.

The indicating device 100 represented on FIG. 6 is for the purpose of indicating the ametropia of wearer at the age of eighteen according to the value of the ametropia at a selected age.

The indicating device 100 includes a first member 120, a second member 140, a third member 160 connected together in translation along the longitudinal axis 200 of the indicating device 100.

Figure 7:
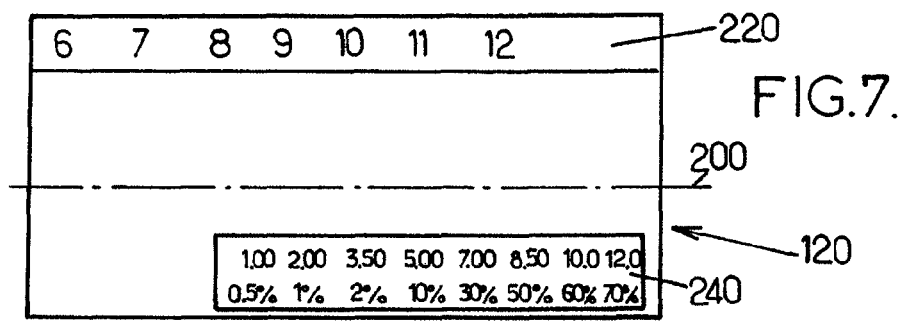
FIG. 7 shows a frontal view of a first member of an indicating device as represented on FIG. 6, FIGS. 8a and 8b show a frontal view of different embodiments of second members of an indicating device as represented on FIG. 6.

FIG. 7 represents an arrangement of the upper face of the first member 120 of an indicating device 100 as represented on FIG. 6. The upper face of the first member 120 comprises a first field 220 comprising a plurality of values of an input data.

The input data may be any type of data that has an impact on the ametropia progression. The input data represented in the first field 220 may be selected among the following list consisting of:

the age of the first optical correction,
the ethnic group of the wearer,
the medical treatment the wearer may use,
the number of reading hours per day,
the reading distance of the wearer,
the type of lighting the wearer may use,
the actual age of the wearer, and
the actual refraction value of the wearer.

According to the embodiment of the invention represented on FIG. 7, the input data represented in the first field 220 represent the age of the wearer.

The upper face of the first member 120 also comprises a second field 240 comprising a plurality of values of output data.

The output data may be any type of data that may be related to the ametropia of a wearer. The output data represented in the second field 240 may be selected among the following list consisting of:
- the ametropia value after a given period of time, for example the ametropia at the age of eighteen,
- the risk of eye pathology,
- the risk of car accident, and
- the risk of falling.

According to the embodiment of the invention represented on FIG. 7, the output data represented in the second field 240 represent the ametropia value and the risk of eye pathology of the wearer at the age of eighteen.

The first 220 and second 240 fields are placed on either part of the longitudinal axis 200 of the indicating device 100.

Figure 8A:
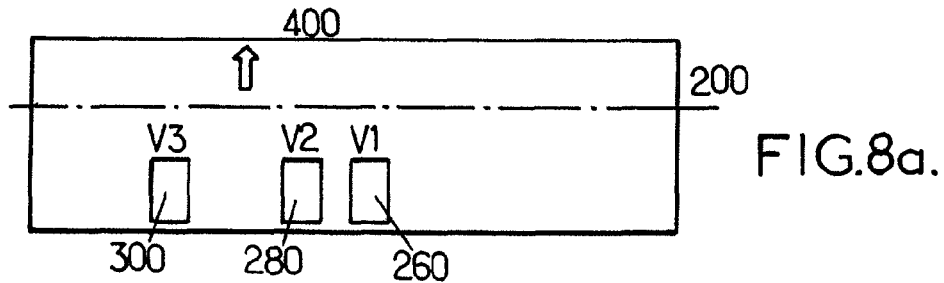
Figure 8B:
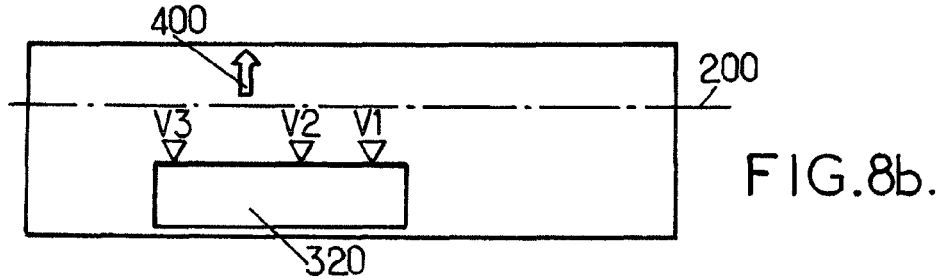

FIGS. 8a and 8b represent two arrangements of the upper face of the second member 140 of an indicating device 100 as represented on FIG. 6.

The upper face of the second member 140 represented on FIG. 8a comprises a first 260, second 280 and third 300 windows. The windows 260, 280, 300 are spaced from the longitudinal axis 200 of the indicating device 100 by a transversal distance which is substantially the same as the transversal distance of the second field 240 of the first member 120. The first 260, second 280 and third 300 windows correspond to different type of ophthalmic lenses the wearer may use.

Alternatively as represented on FIG. 8b, the upper face of the second member 140 may comprise a large window 320.

The large window 320 is spaced from the longitudinal axis 200 of the indicating device 100 by a transversal distance which is substantially the same as the transversal distance of the second field 240 of the first member 120. The upper face of the second member may also comprise first, second and third arrows pointing a specific part of the large window 320 in transversal directions. The first, second and third arrows correspond to different type of ophthalmic lenses the wearer may use.

The upper face of the second member 140 also comprises a fourth arrow 400 pointing to the outer part of the second member 140.

The windows 260, 280, 300 and 320 and the arrows 340, 360, 380 correspond to indication means associated with a type of ophthalmic lens and are arranged so that when the fourth arrow 460 indicates an input value, the output values corresponding to the different ophthalmic lenses are displayed in the windows and/or pointed by the first, second and third arrows.

Figure 9:
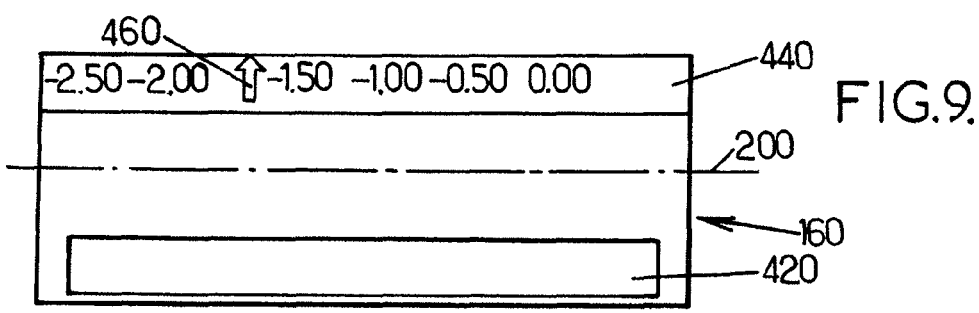
FIG. 9 shows a frontal view of a third member of an indicating device as represented on FIG. 6.

As represented on FIG. 9, the third member 160, comprises a single composite window 420, a field 440 and a selecting mean 460.

The single composite window 420 is spaced from the longitudinal axis 200 of the indicating device 100 by a transversal distance which is substantially the same as the transversal distance of the second field 240 of the first member 120.

The field 440 is part of a longitudinal region of the upper face of the third member 440. The second field 240 is closer to the longitudinal axis 200 than the first field 220. The field 440 comprises a plurality of values of an input data selected among the same list as the input data of the first field 220 of the first member 120.

As represented on FIG. 9, the selecting mean 460 may be an arrow pointing in the outer direction of the third member 160.

According to an embodiment of the invention, the second field 240 and the indication means 260, 280, 300, 320, 340, 360, 380 of the second member 140 are arranged so that the ratio between the value of the output data represented in the second field 240 of the first member 120 corresponding to a first type of ophthalmic lenses and the value of the output data represented in the second field 240 of the first member 120 corresponding to a second type of ophthalmic lenses is constant independently of the value of the input data selected by the selection means 400 and 460.

According to an embodiment of the invention not represented, the indicating device may comprise only the first and second members.

The outer face of the different members or discs may be printed with additional explanatory material and/or promotional material.

The invention has been described above with different embodiments without limitation of the general inventive concept.

The invention claimed is:

1. An indicating device for indicating the ametropia progression of a wearer over a predetermined period of time as a function of the wearer's age according to at least the type of ophthalmic lens the wearer may use, wherein
   the device comprises first and second members connected together in a moveable manner, and a third member connected to the first and second members in a moveable manner,
   the first member having a first field including a plurality of values of input data and a second field including a plurality of values of output data representative of the ametropia of a wearer,
   the second member having at least a selection means and an indication means,
   the selection means being arranged to select among movement of the second member a value of the input data corresponding to a wearer, and
   the indication means being associated with a type of ophthalmic lens and arranged to indicate among movement of the second member the value of the output data on the first member corresponding to the ametropia of the wearer after the predetermined period of time, and
   wherein the third member comprises:
   a field including a plurality of values of second input data,
   a selecting means arranged to select among movement of the third member a value of the input data from the first member, and
   an opening arranged to display at least a part of the second field of the first member among movement of the third member, wherein the ametropia progression of the wearer is a function of the wearer's age.

2. The indicating device according to claim 1, wherein the input data are selected among one or a combination of the following data consisting of:
   the age of the first optical correction,
   the ethnic group of the wearer,
   the medical treatment the wearer may use,
   the number of reading hours per day,
   the reading distance of the wearer,
   the type of lighting the wearer may use,
   the actual age of the wearer, and
   the actual refraction value of the wearer.

3. The indicating device according to claim 1, wherein the output data are selected among one or a combination of the following data consisting of:
the ametropia value after a given period of time,
the risk of eye pathology,
the risk of car accident, and
the risk of falling.

4. The indicating device according to claim 1, wherein the selection means and/or indication means comprise a window dimensioned for displaying a single value of the input data and/or output data.

5. The indicating device according to claim 1, wherein the selection means and/or indication means comprise an arrow arranged to displaying a single value of the input data and/or output data.

6. The indicating device according to claim 1, wherein the first, second and third members are connected together for rotating about an axis.

7. The indicating device according to claim 1, wherein the first, second and third members are connected together for translation about a longitudinal axis of the indicating device.

\* \* \* \* \*